United States Patent
Taguchi

(10) Patent No.: US 10,668,181 B2
(45) Date of Patent: Jun. 2, 2020

(54) SURGICAL SEALANT

(71) Applicant: NATIONAL INSTITUTE FOR MATERIALS SCIENCE, Tsukuba-shi, Ibaraki (JP)

(72) Inventor: Tetsushi Taguchi, Tsukuba (JP)

(73) Assignee: NATIONAL INSTITUTE FOR MATERIALS SCIENCE, Tsukuba-shi, Ibaraki (JP)

(*) Notice: Subject to any disclaimer, the term of this patent is extended or adjusted under 35 U.S.C. 154(b) by 0 days.

(21) Appl. No.: 16/071,625

(22) PCT Filed: Jan. 11, 2017

(86) PCT No.: PCT/JP2017/000675
§ 371 (c)(1),
(2) Date: Jul. 20, 2018

(87) PCT Pub. No.: WO2017/126390
PCT Pub. Date: Jul. 27, 2017

(65) Prior Publication Data
US 2019/0336642 A1  Nov. 7, 2019

(30) Foreign Application Priority Data
Jan. 20, 2016 (JP) ................. 2016-009257

(51) Int. Cl.
*A61L 24/00* (2006.01)
*A61L 24/10* (2006.01)
*C09J 189/00* (2006.01)

(52) U.S. Cl.
CPC ......... *A61L 24/104* (2013.01); *A61L 24/0005* (2013.01); *A61L 24/102* (2013.01); *C09J 189/00* (2013.01)

(58) Field of Classification Search
None
See application file for complete search history.

(56) References Cited

U.S. PATENT DOCUMENTS 5,583,114 A * 12/1996 Barrows ............... A61L 24/043
424/179.1
9,499,728 B2 * 11/2016 Taguchi ................. C09J 189/00
(Continued)

FOREIGN PATENT DOCUMENTS

| JP | H10-503102 A | 3/1998 |
|---|---|---|
| JP | H11-137662 A | 5/1998 |

(Continued)

OTHER PUBLICATIONS

Matsuda et al, bioadhesion of gelatin films crosslinked with glutaraldehyde, journal of biomedical materials research, 45, 1, pp. 21-27 (Year: 1999).*

(Continued)

*Primary Examiner* — Stefanie J Cohen
(74) *Attorney, Agent, or Firm* — Liang Legal Group, PLLC

(57) ABSTRACT

A surgical sealant consisting of (1) a first agent comprising a gelatin derivative, wherein the gelatin derivative (a) has a weight average molecular weight of from 10,000 to 50,000; (b) has a hydrophobic group bonded thereto, the hydrophobic group being an alkyl group having 6 to 18 carbon atoms; (c) has a molar ratio of imino group/amino group of the gelatin derivative ranging from 1/99 to 30/70; and (d) comprises a structure represented by the following formula: GltnNH—CHR$^1$R$^2$, wherein "Gltn" represents a gelatin residue, R$^1$ is the hydrophobic group, and R$^2$ is a hydrogen atom or the hydrophobic group; and (2) a second agent comprising a crosslinking agent for the gelatin derivative.

7 Claims, 8 Drawing Sheets

(56) References Cited

U.S. PATENT DOCUMENTS

| | | | |
|---|---|---|---|
| 10,420,855 B2 * | 9/2019 | Taguchi | A61L 24/00 |
| 2002/0155398 A1 * | 10/2002 | Yanagi | G03C 1/0051 |
| | | | 430/567 |
| 2011/0129640 A1 * | 6/2011 | Beall | B28B 1/001 |
| | | | 428/116 |
| 2013/0220174 A1 * | 8/2013 | Taguchi | A61L 24/104 |
| | | | 106/155.21 |

FOREIGN PATENT DOCUMENTS

| | | |
|---|---|---|
| JP | 2003-000695 A | 1/2003 |
| WO | 2012/046717 A1 | 4/2012 |
| WO | 2014/112208 A1 | 7/2014 |

OTHER PUBLICATIONS

Sarika et al, modified gum arabic cross-linked gelatin scaffold for biomedical applications, materials science and engineering C, 43, 272-279 (Year: 2014).*

Ryo Mizuta et al., Sealing effect of Hydrophobically modified, pollock gelatin with different alkyl chain length, The Adhesion Society of Japan, 53th Annual Conference, Abstract, Jun. 5, 2015, pp. 52-53. (cited in International Search Report, D2).

International Search Report, PCT/JP2017/000675.

* cited by examiner

Hydrophobically modified gelatin after electron beam irradiation

Viscosity change of solution by electron beam sterilization unit: mPa·S

| Sample | EB- | EB+ | | |
|---|---|---|---|---|
| | | 20kGy | 40kGy | 60kGy |
| Example 6 (380,000 7.2C12) | 21.5 | 20.4 | 32.1 | 54.8 |
| Example 4 (240,000 13C12) | 28 | 53.0 | 55.7 | 72.9 |

(15w/v%0.1Mborate buffer pH9)

SURGICAL SEALANT

TECHNICAL FIELD

The present invention relates to a surgical sealant, specifically to a surgical sealant comprising a gelatin derivative having a hydrophobic group as a base material.

BACKGROUND OF THE INVENTION

A surgical sealant or tissue adhesive (hereinafter collectively referred to as "sealant") is a material, which is applied to an anastomosed part among tissues or a damaged portion of a living body to form a sealant membrane, thereby preventing leakage of blood or air. It is used in various surgeries, such as respiratory surgery, gastrointestinal surgery, cardiovascular surgery, oral surgery or the like. The most widely used sealant nowadays is a fibrin sealant (Bolheal® produced by Kaketsuken). The sealant has an excellent biocompatibility but has a problem of relatively low adhesion to the tissue and low sealing strength of an affected part. The sealing strength as used herein is measured as pressure-resistant strength or burst strength of the membrane, for which both strength of the membrane itself and adhesion strength of the membrane to living tissues are required.

To solve the aforesaid problem, the present inventor has been developing a sealant comprising a gelatin having a hydrophobic group, hereinafter may be referred to as "hydrophobically modified gelatin" (for example, Patent document 1, and Patent document 2). The membrane obtained from the sealant has a higher adhesion and sealing strengths and less swelled by body fluid.

However, in addition to the properties as mentioned above, it is important for a biological material to have the sterilization resistance in the form of a final product, that is, packed in a final container or package. The Japanese Pharmacopoeia specifies that a final sterilization method should be selected from thermal method, radiation method, and gaseous method (The Japanese Pharmacopoeia, Fourteenth Edition, Part II, the reference information, page 1235). The aforesaid fibrin sealant is sterilized by the thermal method, but it is not applicable to the hydrophobically modified gelatin because a molecular weight thereof is decreased by hydrolysis. The gaseous method is not applicable, either, because the hydrophobically modified gelatin is typically used in the form of an aqueous solution. Consequently, the radiation method is to be used, but it is very difficult to sterilize a material mainly composed of protein such as gelatin without denaturing.

For example, Patent document 3, which relates to a radiation sterilization of a collagen gel, describes that the radiation sterilization significantly impair properties of the collagen gel by causing a partial crosslinking and decomposition reactions (Patent document 3, paragraph [0005]) and proposes adding to the collagen gel a radiation protective agent, such as a heat-denatured atelocollagen. In addition, a method of irradiating a polymer such as gelatin by blending a polyfunctional triazine compound in the polymer (Patent Document 4)

PRIOR ART DOCUMENTS

Patent Document

[Patent Document1] WO2012/046717
[Patent Document2] WO2014/112208
[Patent Document3] Japanese Patent Application Laid-Open No. 11-137662
[Patent Document4] Japanese Patent Application Laid-Open No. 2003-695

SUMMARY OF THE INVENTION

Problems to be Solved by the Invention

However, the addition of the denatured atelocollagen degrades properties of a sealant membrane. The polyfunctional triazine compound significantly degrades fluidity required for the sealant to apply to an affected site because the addition thereof prevents the polymer from degradation through formation of molecular crosslinkage between polymer chains.

Thus, an object of the present invention is to provide a surgical sealant that can be sterilized without adding a radiation protective agent. Yet another object of the present invention is to provide a surgical sealant that can be produced in a simple manner and safely.

Means to Solve the Problem

The present invention is a surgical sealant consisting of
(1) a first agent comprising a gelatin derivative, wherein the gelatin derivative
  (a) has a weight average molecular weight of from 10,000 to 50,000;
  (b) has a hydrophobic group bonded thereto, the hydrophobic group being an alkyl group having 6 to 18 carbon atoms;
  (c) has a molar ratio of imino group/amino group of the gelatin derivative ranging from 1/99 to 30/70; and
  (d) comprises a structure represented by the following formula:

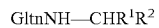

GltnNH—CHR$^1$R$^2$ wherein "Gltn" represents a gelatin residue, R$^1$ is the hydrophobic group, and R$^2$ is a hydrogen atom or the hydrophobic group; and
(2) a second agent comprising a crosslinking agent for the gelatin derivative.

Effects of the Invention

The aforesaid sealant has an excellent radiation resistance by comprising a base material having a predetermined molecular weight and the hydrophobic group. A membrane obtained from the sealant has a higher adhesion strength to tissues and sealing strength of tissues with less swelling by body fluids. Further, the sealant can be produced in an aqueous medium and thus achieves safety in the manufacturing environment and in the body. In addition, it can be simply produced in one-step process with a high yield.

DETAILED DESCRIPTION

The surgical sealant of the present invention is a two-component type sealant consisting of a first agent comprising a gelatin derivative, which substantially constitutes the sealant, and a second agent comprising a crosslinking agent for the gelatin derivative. The first agent and the second agent are packed separately and are mixed in use. The following describes details thereof <The First Agent>

Figure 1:
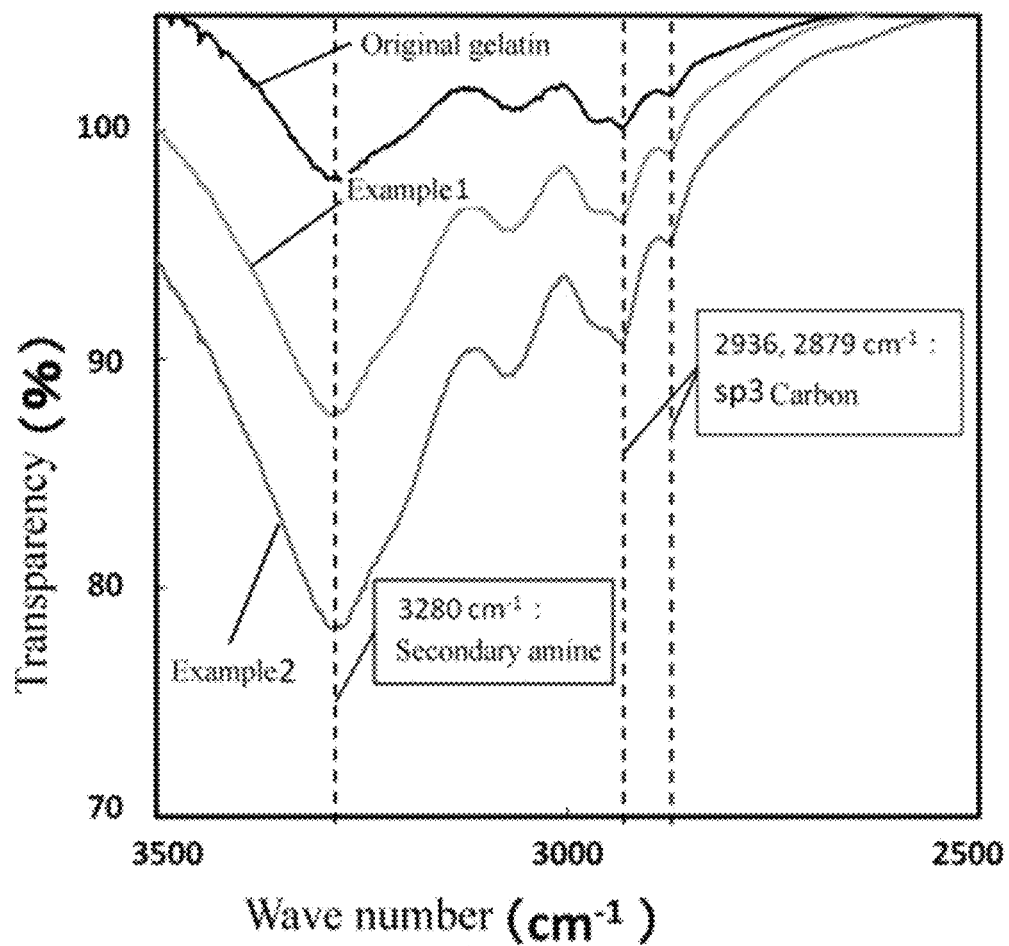
FIG. 1 is FT-IR spectra of an original gelatin derived from Alaska pollock, and gelatin derivatives of Examples 1 and 2.

In a surgical sealant of the present invention, the first agent comprises a gelatin derivative. The gelatin derivative has a hydrophobic group bonded via an imino group, that is —NH—, to have a structure represented by the following formula:

wherein "Gltn" represents a gelatin residue, $R^1$ is the hydrophobic group, and $R^2$ is a hydrogen atom or the hydrophobic group. In the above structure, "N" mainly originates from ε-amino group of lysine (Lys) in the gelatin. Preferably, $R^2$ is a hydrogen atom. The NH structure in the formula (1) can be identified by, for example, an absorption band around 3300 cm$^{-1}$ in FT-IR spectrum. FIG. 1 shows FT-IR spectra of the gelatin derivatives of Examples 1 and 2 described later with a spectrum of the original gelatin for comparison. It can be seen that N—H vibration around 3300 cm$^{-1}$ and C—H vibration around 2900 cm$^{-1}$ become stronger with an increased amount of hydrophobic group.

When $R^2$ is a hydrophobic group, it may be the same as or different from R'. The hydrophobic group is an alkyl group having 6 to 18 carbon atoms, which may be branched. Examples of the alkyl group include hexyl group, octyl group (or caprylic group), nonyl group (or pelargonyl group), dodecyl group (or lauryl group), tetradecyl croup (or myristyl group). Preferably, $R^1$ is an alkyl group having 8 to 14 carbon atoms, and $R^2$ is a hydrogen atom.

A ratio of derivatization in the gelatin derivative is defined as a mol % of the imino group, to which the hydrophobic group bonded, to the amino group in the original gelatin, and ranges from 1 to 30 mol %, preferably from 5 to 10 mol %. In other words, a molar ratio of imino group/amino group in the obtained gelatin derivative ranges from 1/99 to 30/70, preferably from 5/95 to 10/90. The ratio of derivatization can be determined by quantifying the amino group of the original gelatin and that of the gelatin derivative through titration with an acid such as hydrochloric acid, or by a quantitative identification of the hydrophobic group with NMR, or the like.

The gelatin derivative has a weight average molecular weight (Mw) of from 10,000 to 50,000, preferably from 10,000 to 40,000. In the range, an excellent resistance to electron beam sterilization is observed. The molecular weight can be determined by gel permeation chromatography (GPC) according to a conventional procedure.

The original gelatin may be of natural origin, chemically synthesized, fermented, or genetically modified gelatin. Preferably, a gelatin of natural origin is used, such as bovine, porcine, or fish gelatin, more preferably cold-water fish gelatin, such as sea bream or codfish gelatin, and most preferably codfish gelatin, particularly Alaska pollack gelatin. The cold-water fish gelatin contains less imino acid than the porcine gelatin, so that it can make a sealant having a good fluidity at room temperature even at a high concentration thereof.

The original gelatin may be an acid-treated gelatin or an alkaline-treated gelatin. Preferably, it is an alkaline-treated gelatin. A molecular weight thereof may be in a range such that the gelatin derivative has an average molecular weight (Mw) in the aforesaid range.

The first agent may comprise non-derivatized gelatin in addition to the gelatin derivative. As the gelatin, the aforesaid various kinds of gelatin may be used. The non-derivatized gelatin may be contained in an amount of from 0 to 99 wt %, preferably 0 to 50 wt % of a total weight of the derivatized and the non-derivatized gelatin.

The first agent may further comprise an aqueous solvent to dissolve or disperse the gelatin derivative. From the convenience viewpoint, the gelatin derivative may be provided in the form of an aqueous liquid, hereinafter may be simply referred to as "aqueous solution." The aqueous solvent may be ultrapure water, saline, buffer solution containing acid, such as boric acid, phosphoric acid, or carbonic acid, and a salt thereof, or a mixture of these solvents. Preferably, a borate buffer having a pH of from 8 to 11, preferably from 9 to 10 is used. The aqueous solvent is used in such an amount that a concentration of the gelatin derivative ranges from 10 to 80 wt/v %, preferably from 15 to 30 wt/v %. When the non-derivatized gelatin is contained, a total concentration of the gelatin derivative and non-derivatized gelatin falls in the aforesaid concentration.

<Second Agent>

In the present invention, the second agent is a crosslinking agent for the gelatin derivative, which forms a structure, for example, a membrane insoluble in water or body fluids such as blood. At least one kind of crosslinking agent is used which has at least two functional groups per molecule reactive with the amino groups in gelatin, mainly the primary amino group at side chains. Examples of the crosslinking agent include genipin, polybasic acids activated with N-hydroxysuccinimide or N-hydroxysulfosuccinimide, aldehyde compounds, acid anhydrides, and diisothiocyanates.

Examples of the polybasic acid include tartaric acid, citric acid, malic acid, glutaric acid, glutamic acid, aspartic acid, oxaloacetic acid, cis-aconitic acid, 2-ketoglutaric acid, poly-tartaric add, polycitric acid, polymalic acid, polyglutamic add, polyaspartic acid, carboxymethylated dextrin, carbon/ methylated dextran, carboxymethylated starch, carboxymethylated cellulose, carboxymethylated chitosan, carboxymethylated pullulan, and active-esterified derivatives thereof such as disuccinimidyl glutarate (USG), disuccinimidyl suberate (DSS), and disuccinimidyl tartrate (DST).

Other examples of the polybasic acid include polybasic acid esters of polyethylene glycol or polyethylene glycol ethers with at least one carboxyl group, which is not reacted with polyethylene glycol, being active esterified such as 4,7,10,13,16 penta-oxanonadecanoic acid di (N-succinimidyl), and polyethylene glycol di(succinimidyl succinate) (SS-PEG-SS represented by the following formula:

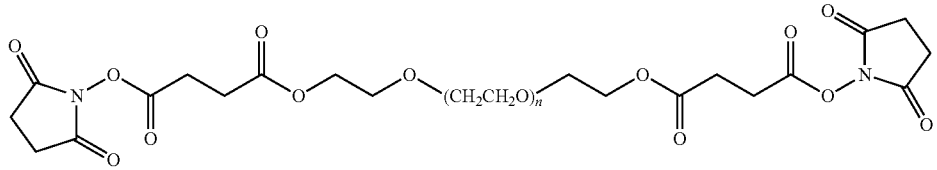

wherein n is such a number that Mw ranges from about 10,000 to 20,000; and
pentaerythritol polyethylene glycol ether tetrasuccinimidyl glutarate (4S-PEG) represented by the following formula:

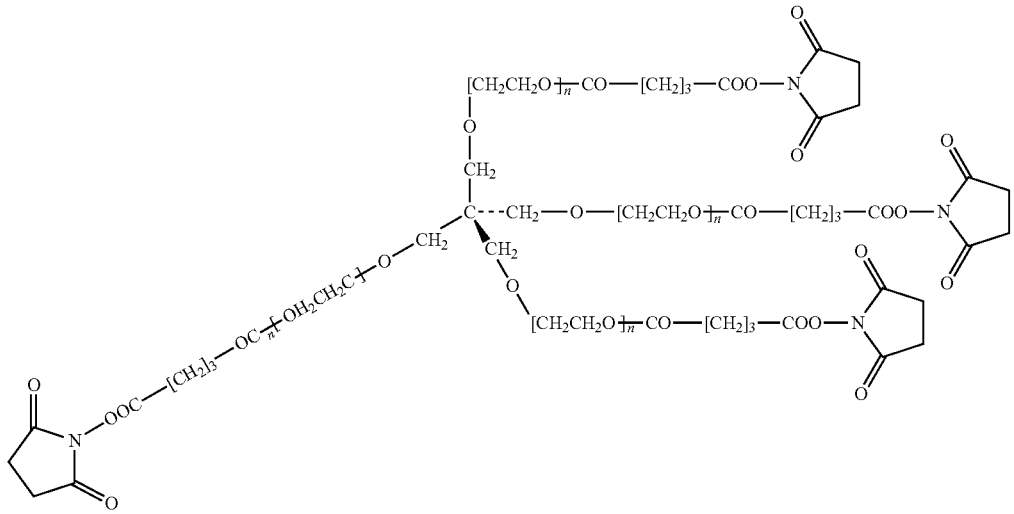

wherein n is such a number that Mw ranges from about 3,000 to 30,000, preferably from about 5,000 to 27,000, more preferably from about 10,000 to 20,000.

Examples of the aldehyde compounds include aldehyde group-introduced polysaccharides, such as aldehyde group-introduced starch, aldehyde group-introduced dextran, aldehyde group-introduced dextrin, and aldehyde group-introduced hyaluronic acid. Examples of the acid anhydride include glutaric acid anhydride, maleic acid anhydride, and succinic acid anhydride. Example of diisocyanate includes hexamethylene diisothiocyanate. Among these, aforesaid activated polybasic acid ester of polyethylene glycol, and aldehyde group-introduced polysaccharides are preferably used.

These crosslinking agents are used in such an amount that a functional group, for example, an ester group activated with N-hydroxysuccinimide, in the crosslinking agents per one mole of the amino group of the gelatin derivative ranges from 0.2 to 3 equivalents, preferably from 0.2 to 2 equivalents, more preferably from 0.4 to 1.2 equivalents, and most preferably from 0.2 to 0.5 equivalent. A mixture of two or more kinds of the crosslinking agents may be used in such an amount that a total equivalent amount thereof falls in the above range.

The second agent may comprise an aqueous solvent to dissolve the crosslinking agent, too. It should be noted that preferably the crosslinking agent and the aqueous solvent are provided in separate containers, and at most about 2 hours before the use adequate amounts thereof are mixed into an aqueous solution, which may be hereinafter referred to as "aqueous solution." As the aqueous solvent, the aqueous solvents mentioned above for the first agent can be used. Preferably, a phosphate buffer having a pH of from 3 to 8, more preferably from 4 to 6, is used. Most preferably, ionic strengths of both aqueous solvents are adjusted so that a mixture of the same volume of the first agent solution and the second agent solution has a pH of from 8 to 9. For example, an aqueous solution of the first agent in a borate buffer having a pH of 9 and an ionic strength of 0.05 to 0.1, and an aqueous solution of the second agent in a phosphate buffer having a pH of 4 and an ionic strength of from 0.01 to 0.03 can make an equivolume mixed solution having a pH of from 8 to 9. Another example is a combination of an aqueous solution of the first agent in a borate buffer having a pH of 10 and an ionic strength of 0.05 to 0.1, and an aqueous solution of the second agent in a phosphate buffer having a pH of 4 and an ionic strength of from 0.01 to 0.07.

A concentration of the second agent is adjusted so that an equivalent amount of a functional group of the second agent relative to an equivalent amount of the amino group in the first agent, i.e., (an equivalent amount of a functional group of the second agent/an equivalent amount of the amino group in the first agent), falls in the range mentioned above. A mixture of two or more kinds of the crosslinking agents may be used in such an amount that a total amount thereof falls in the aforesaid range.

<Additives>

The first agent and/or the second agent may comprise various additives in such an amount that they do not adversely affect the sealant of the present invention. Examples of the additives include colorants, pH adjusting agents, viscosity modifiers, and preservatives or the like. Preferably, in order to highlight the applied site, an aqueous solution of the first agent or the second agent comprises a colorant such as brilliant blue in an amount of from 10 to 100 µg/mL, for instance.

<Manufacturing Method>

A sealant of the present invention can be produced by preparing the first agent and the second agent, packaging, and then sterilizing separately.

[Preparation of the First Agent]

(1) Preparation of an Aqueous Solution of an Original Gelatin

A starting original gelatin is dissolved in an aqueous solvent at a concentration of from 5 to 50 wt/v % by heating at 40 to 90° C. The aqueous solvent may be a mixture of water and water soluble organic solvent. Examples of the organic solvent include an alcohol having 1 to 3 carbon atoms and esters having 1 to 3 carbon atoms, and preferably ethanol is used.

(2) Derivatization

To the aqueous solution of the gelatin obtained in the step (1), a derivatizing agent having a hydrophobic group to be introduced to the gelatin is added and a mixture thus obtained is subjected to a reaction while stirring for a predetermined period of time. As the derivatizing agent, an aldehyde or a ketone having the hydrophobic group is used such as dodecanal, tetradecanal, and decyl ethyl ketone. A reaction temperature ranges from 30 to 80° C., and a reaction time ranges from 0.5 to 12 hours. A gelatin derivative having an alkyl group bonded to an amino group of the gelatin in the form of a Shiff base ($GltnN=CR^1R^2$) can usually be obtained merely by stirring. The aldehyde is used in an amount of from 1 to 4 times, more preferably from 1 to 2 times, the stoichiometric amount corresponding to a desired derivatization ratio.

Subsequently, the Shiff base is reduced to the structure of the above formula (1). A known reducing agent can be used, such as sodium cyanoborohydride ($NaBH_3CN$), sodium triacetoxyborohydride ($NaBH(OAc)_3$), 2-picoline borane, and borane, among which 2-picoline borane is preferred. The 2-picoline borane is stable to allow a one-pot reductive amination reaction of aldehydes or ketones in an aqueous solvent. In addition, a yield of from 80 to 90% can be achieved, which is significantly higher than 70 to 75? achieved by sodium cyanoborohydride. Preferably, 2-picoline borane is used in an amount of from 1 to 3 equivalents relative to an equivalent of a derivatizing agent.

(3) Purification

To the reaction solution from the step (2), a large excess amount of a poor solvent such as cold ethanol is added to precipitate a gelatin derivative. After isolating the precipitate by filtration, it is washed with ethanol or the like to obtain a final product.

(4) Preparation of the First Agent

The gelatin derivative obtained in the step (3) is provided in the form of powder or aqueous solution in an aqueous solvent, such as borate buffer, and is packed in a container. Examples of the container include glass or plastic vial, bottle, dispenser, and syringe. The non-derivatized gelatin or the additives may be incorporated as desired. When the gelatin derivative is provided in the form of powder, an aqueous solvent such as a borate buffer is provided in a separate container. When the gelatin derivative is provided in the form of an aqueous solution, it may be placed in one of the syringes of a dual syringe dispenser which can mix two agents at a tip thereof which is used to apply the surgical sealant to an affected part. Needless to say, a surgical sealant of the present invention can comprise as an accessory, a dual syringe dispenser, a vial for mixing, and a spare aqueous solvent.

[Preparation of the Second Agent]

The above crosslinking agents described as the examples of the second agent may be synthesized by known methods or purchased. The crosslinking agent and an aqueous solvent to dissolve it are provided in separate containers, for example, the crosslinking agent in a glass vial and the aqueous solvent in a plastic bottle. Additives may be added as desired. The first agent and the second agent are provided in such an amount that a ratio, (an equivalent amount of functional group of the crosslinking agent/an equivalent amount of amino group in the gelatin derivative), ranges from 0.2 to 2, but the first agent and the second agent may be provided in such a manner that each agent can be replenished independently.

<Radiation Sterilization>

Subsequently, the first agent in the form of an aqueous solution packed in a dispenser or in the form of a combination of the gelatin derivative powders packed in a vial and an aqueous solvent in a bottle, and the second agent in the form of a combination of the crosslinking agent powder packed in a vial and an aqueous solvent to dissolve the crosslinking agent in a bottle are radiation sterilized. The radiation may be electron beams, gamma rays, or bremsstrahlung, among which electron beam sterilization is preferred. A total absorbed dose may be at least 20 kGy, which is widely employed (Japanese Pharmacopoeia, Fourteenth Edition, Part Two, Reference information, page 1235, right column, 2.2 Radiation Method), preferably ranges from 25 kGy to 45 kGy. To avoid damages of the gelatin derivative or the crosslinking agent, a multiple irradiation may be performed as far as a total absorbed dose is at least 20 kGy. For example, an irradiation at 6 kGy may be repeated five times in place of one sterilization of 30 kGy. As shown in Examples described later, a surgical sealant of the present invention is resistant to irradiation sterilization at 60 kGy.

<Method of Application to the Tissues>

The present invention encompasses a method of forming a sealant membrane comprising the step of applying the first agent and the second agent to an affected site of a human or an animal subject, and a method of treating a subject comprising the step of forming a sealant membrane. The surgical sealant of the present invention can be applied to a ruptured site of the skin, blood vessels, tendons, nerves, the intestine, a tubular tissue such as the lymph vessel, and organs such as the liver, the pancreas, and the heart, particularly suitable to wet tissues such as blood vessels and the lungs. The surgical sealant may be applied firstly by dissolving the second agent into an aqueous solution preferably just prior to the use as mentioned above. A concentration of the crosslinking agent is as described above. Then, thus obtained aqueous solution of the second agent may be placed in a vacant syringe of a dual syringe dispenser, of which other syringe is filled with an aqueous solution of the first agent, and the first and the second agent are applied or sprayed by an air-assisted spray to an affected site of a subject. After several minutes to 10 minutes of the application, a sealant membrane is formed to seal the site.

EXAMPLES

The present invention will be explained with reference to the Examples, but the present invention is not limited thereto.

Figure 2:
FIG. 2 is a photograph of a 20 w/v % solution of an original gelatin having a weight average molecular weight (Mw) of 13,000 to 94,000 in 0.1M borate buffer (pH 9) after it was electron beam sterilized at a total absorbed dose of 10 to 40 kGy.

Fundamental Experiment 1: Effects of Molecular Weight of Gelatin on Resistance to Radiation Sterilization Using Alaska pollack-derived gelatins (produced by Nitta Gelatin Inc.) having various weight average molecular weight (Mw), influences of molecular weight on resistance to electron beam sterilization was studied. The gelatin was dissolved at a concentration of 20 w/v % in 0.1M borate buffer (pH 9) by heating at 80° C. for 20 minutes. The solution thus obtained was sterilized with electron bean at a total absorbed dose of from 10 to 40 kGy. The results are shown in FIG. 2. As is found from the figure, no degradation was observed for Mw of less than 60,000, and satisfactory resistance to electron beam sterilization was observed for Mw of 38,000 or smaller.

Examples 1-7

<Preparation of the First Agent>

Alaska pollock-derived gelatin (Mw 13,000, produced by Nitta Gelatin Inc.) was dissolved in 350 mL of water, and to the aqueous solution thus obtained 140 mL of ethanol was added and stirred at 50° C. Dodecanal in an amount of about 1.5 equivalents of stoichiometric amount corresponding to the derivatization ratios of amino groups of the gelatin shown in Table 1 was dissolved in 5 mL of ethanol, which was mixed with the gelatin solution. Subsequently, 2-picoline borane in an amount of about 1.5 equivalents of dodecanal was added and stirred for 18 hours. The produced gelatin derivative was precipitated by adding dropwise cold ethanol in an amount of 10 times the volume of the reaction mixture, and then was suction filtered. The obtained filtration residue was placed in cold ethanol in an amount of about 5 times the volume of the residue and washed while stirring for one hour, followed by suction filtration. After repeating this washing process for three times, the product was vacuum dried for 2 days and the gelatin derivative of Example 1 having dodecyl groups was obtained with about 82% yield. The derivatization ratio was determined by a titration method using hydrochloric acid.

The gelatin derivatives shown in Table 1 were prepared in the same manner as described above except that the molecular weight (Mw) of Alaska pollock-derived were varied to 24,000 or 38,000, and tetradecanal in place of dodecanal was used.

TABLE 1

|  | Mw | $R^1$ | $R^2$ | Derivatization ratio (mol %) |
|---|---|---|---|---|
| Example 1 | 13000 | C12 | H | 4.2 |
| Example 2 | 13000 | C12 | H | 8.9 |
| Example 3 | 24000 | C12 | H | 5.4 |
| Example 4 | 24000 | C12 | H | 13 |
| Example 5 | 24000 | C14 | H | 6.2 |
| Example 6 | 38000 | C12 | H | 7.2 |
| Example 7 | 38000 | C14 | H | 4.8 |

Each of the above gelatin derivatives was dissolved in 0.1M borate buffer having a pH of 9 at a concentration of 20 w/v % in Examples 1 and 2, and 15 w/v % in Examples 3 to 7. The solution thus obtained was placed in a 2.5 mL polypropylene disposable syringe and thereby each first agent was obtained.

<Preparation of the Second Agent>

As the second agent, pentaerythritol poly(ethylene)glycol ether tetrasuccinimidyl glutarate (4S-PEG, NOF Co., Ltd.) was used. Just before the characterization described below, 4S-PEG was dissolved in a phosphate buffer having a pH of 4 and comprising 100 μg/mL of brilliant blue. An amount of 4S-PEG was such that a molar equivalent ratio of the succinimidyl ester group thereof to the remaining amino group in the first agent was 0.75 in Examples 1 and 2, and 0.5 in the other Examples. The aqueous solution thus obtained was placed in the same kind of syringe as used for the first agent, and thereby each second agent was obtained.

[Characterization]

<Swelling>

The first and second agents were individually injected in an amount of 200 μl between two glass plates sandwiching a 1 mm-silicone rubber spacer to form a cured sealant. A 1.0 mm-thick circular sealant membrane having a diameter of 15 mm was punched out from the cured sealant. The sealant membrane was immersed in physiological saline at 37° C., and a swelling property of the sealant membrane was observed by a weight change of the sealant membrane with time. In this study, the first agent was in the form of a 0.1M phosphate buffer solution having a pH of 8, and a ratio, (equivalent of succinimidyl ester group in the crosslinking agent/amino group in the gelatin derivative), was 0.75 in Examples 1 and 2, 0.5 in Examples 3-5, and 0.5 in Examples 6 and 7. As a comparative example, the original non-derivatized gelatin was used.

Figure 3:
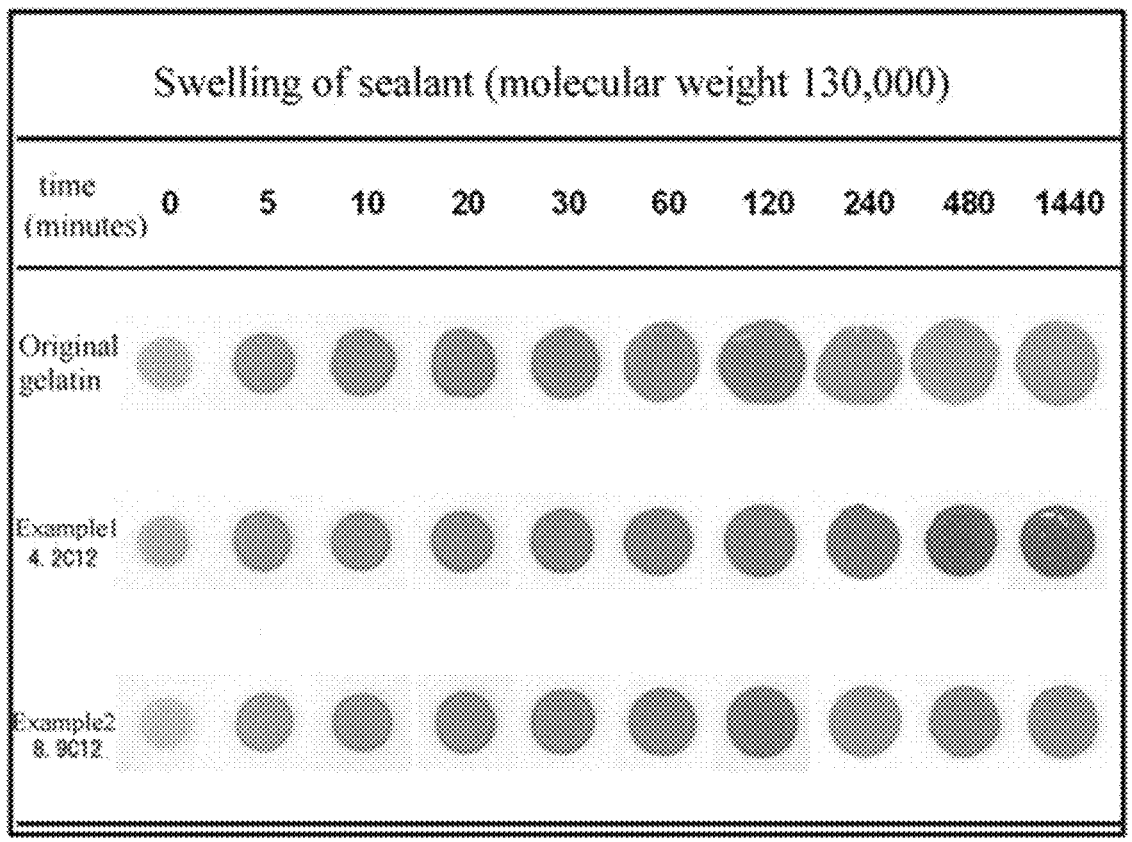
FIG. 3 shows changes over time in swollen state of the original gelatin derived from Alaska pollock, and the sealant membranes of Examples 1 and 2 in saline solution at 37° C.
Figure 4:
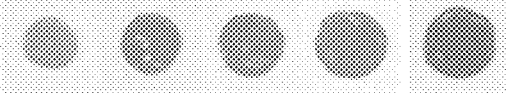
FIG. 4 shows changes over time in swollen state of the original gelatin derived from Alaska pollock, and the sealant membranes of Examples 3 to 5 in saline solution at 37° C.
Figure 5:
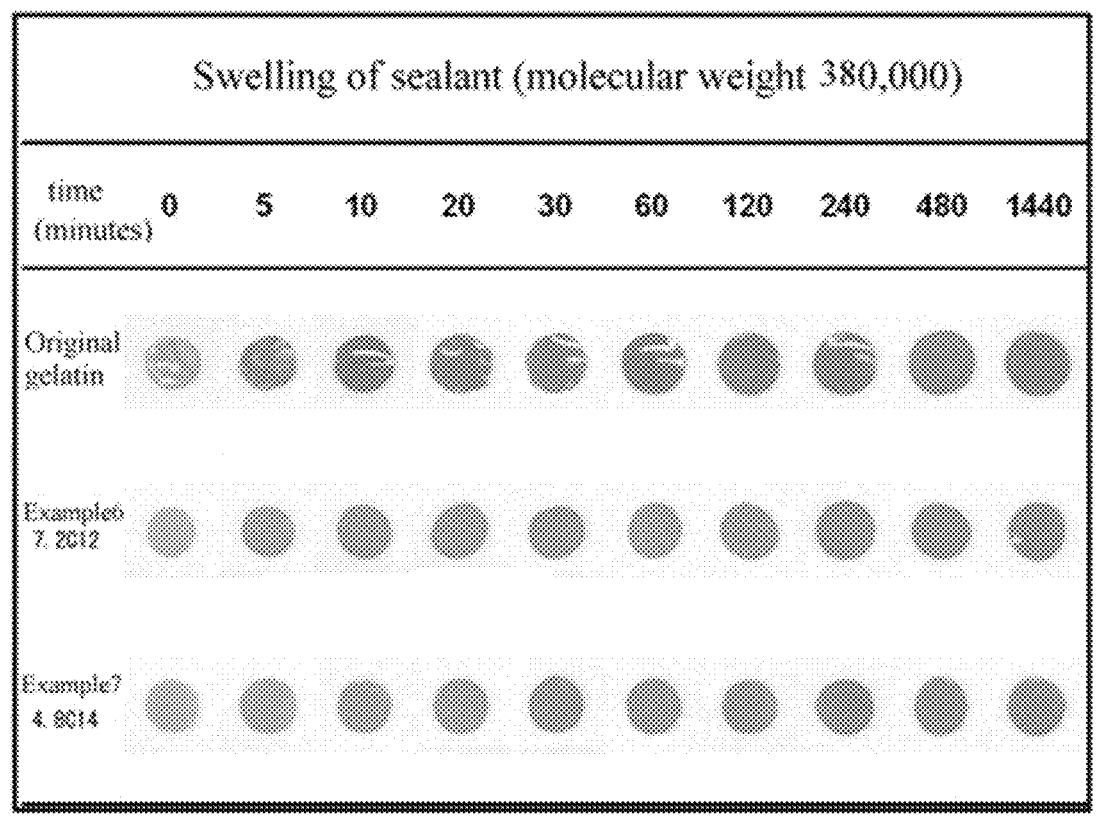
FIG. 5 shows changes over time in swollen state of the original gelatin derived from Alaska pollock, and the sealant membranes of Examples 6 and 7 in saline solution at 37° C.
Figure 6:
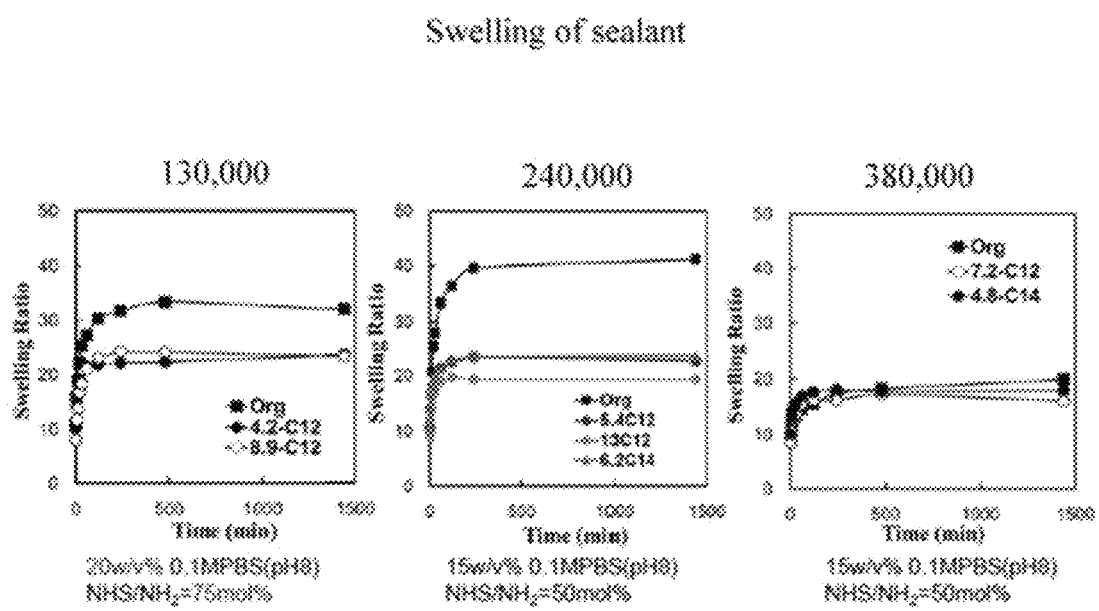
FIG. 6 is a graph of quantized swelling behaviors shown in FIGS. 3 to 5.

FIGS. 3-5 show photographs of the sealant membranes in chronological order, and FIG. 6 shows plotted swelling ratios, ((Swollen weight−Dry weight)/Dry weight). In these figures, the expression, "4.2C12", for instance, represents a gelatin derivatized with dodecyl group at a derivatization ratio of 4.2 mol %. From these results, the swelling property of the sealant membrane is improved by the derivatization with the alkyl group, which is particularly significant in the gelatin having Mw of from 13,000 or 24,000.

<Electron Beam Sterilization of the First Agent>

Figures 7, 8:
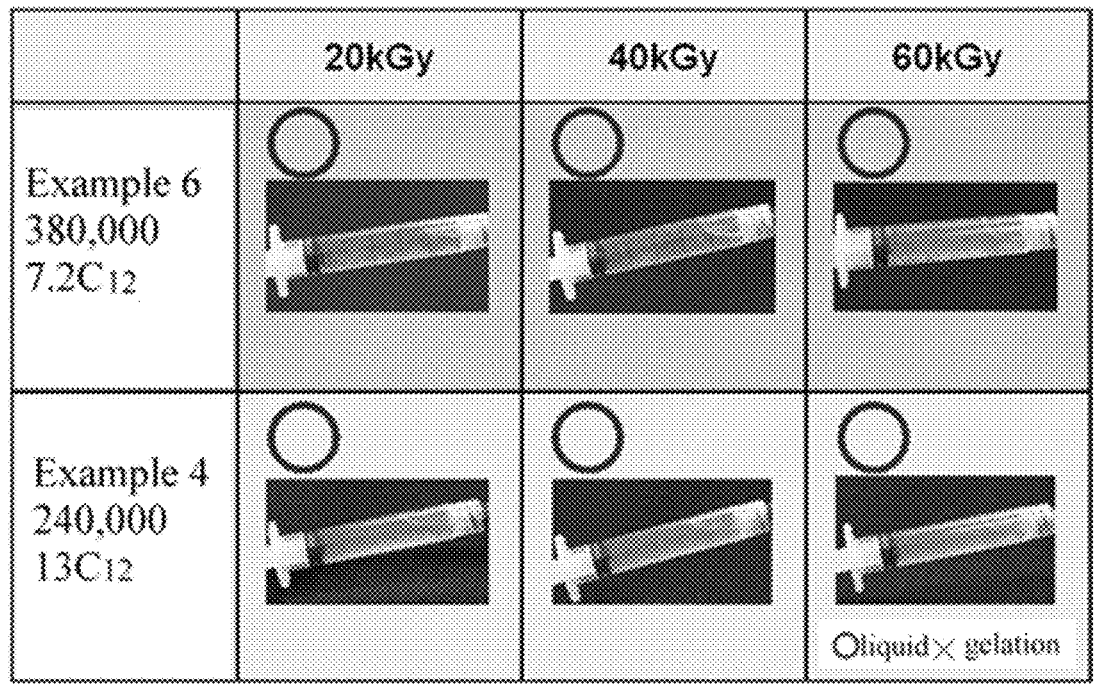
FIG. 7 is a photograph showing changes in fluidity of solutions of the first agent of Examples 4 and 6 in 0.1 M borate buffer (pH9) (20 w/v % of a derivative of gelatin derived from Alaska pollock) by electron beam irradiation with varying total absorbed dose of from 20 to 60 kGy.
FIG. 8 is a table showing changes in viscosity of the first agents of Examples 4 and 6 by electron beam irradiation.

Each of the gelatin derivatives prepared in Examples 4 and 6 was dissolved in 0.1M phosphate buffer at 15 w/v % and placed in 2.5 mL polypropyrene disposable syringe. The syringes were irradiated one time with electron beam at different total absorbed dose of from 20 to 60 kGy, and a degree of degradation was investigated by change in a fluidity of the gelatin derivatives caused by gelation. FIG. 7 shows photographs of the irradiated samples, and FIG. 8 shows viscosities after the irradiation at each total absorbed dose. In FIG. 8, "EB−" represents "before the electron beam irradiation", and "EB+" represents "after the electron beam irradiation."

As shown in FIG. 7, all the gelatin derivatives maintained their fluidity up to 60 kGy. The viscosity was at most 80 mPa·s, so that it was confirmed that they can be applied to an affected site without problem. The original gelatin showed less degradation at a lower molecular weight (FIG. 2), while the gelatin derivative having a molecular weight of 38,000 showed superior resistance to sterilization (FIG. 8).

<Sealing Strength Measurement I>

Figure 9:
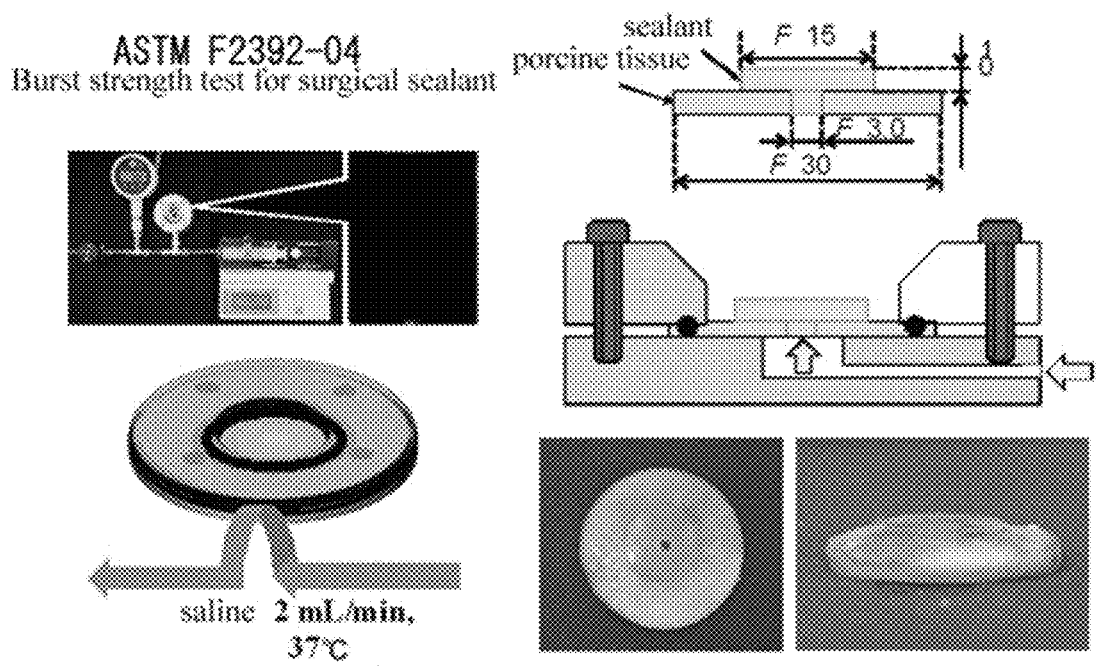
FIG. 9 is a schematic diagram showing a method for measuring a burst strength of a surgical sealant according to the American Standard Test Method (ASTM F2392-04).

A sealing strength (pressure resistance) was measured by determining the burst strength according to ASTM (F2392-04) by using the instrument schematically shown in FIG. 9 and porcine aorta (φ30 mm) as the base material before and after electron beam sterilization at a total absorbed dose of 40 kGy. A 1.0 mm-thick sealant membrane having a diameter of 15 mm was formed on the porcine aorta by applying a mixture of 200 μL of the first agent and 200 μL of the second agent (equivalent of succinimidyl ester group of the crosslinking agent/equivalent of amino group in the gelatin derivative=0.5). Following the application, pressure bonding was performed with a weight of 5.0 g/mm² for 10 minutes. Then, saline at 37° C. was flowed at 2 mL/min and a pressure at bursting was measured. As a comparative example, a commercially available fibrin sealant (Bolheal® produced by Kaketsuken) was used. The results are shown in FIG. 10.

Figure 10:
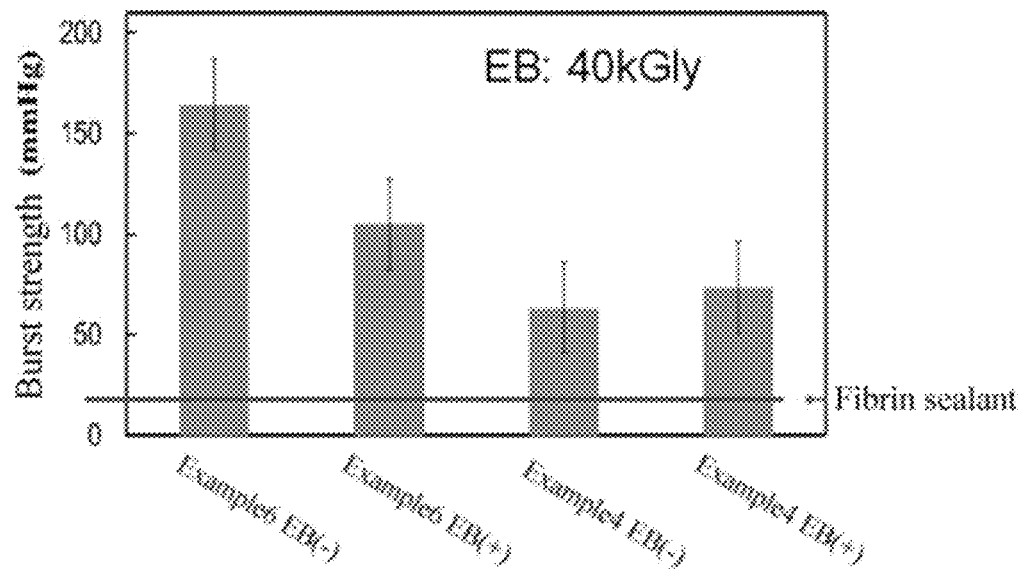
FIG. 10 is a graph showing burst strengths (mmHg) of the sealant membranes of Examples 4 and 6.

As shown in FIG. 10, the sealant of the present invention showed significantly higher sealing strength compared with the fibrin sealant (about 20 mmHg) even after electron beam sterilization. The fibrin sealant exhibited adhesive failure at the interface between the sealant and the porcine aorta, whereas the present sealant exhibited cohesive failure of the sealant itself. These results show that the sealant of the present invention is superior in adhesion strength, too.

Examples 8-10

<Preparation of the First Agent>

The gelatin derivatives shown in Table 2 were prepared in the same manner as in Example 1 except that Alaska pollock-derived gelatin having a molecular weight (Mw) of 35,000, and octanal, decanal, or dodecanal were used.

TABLE 2

| | Mw | R¹ | R² | Derivatization ratio (mol %) |
|---|---|---|---|---|
| Example 8 | 35000 | C8 | H | 4.5 |
| Example 9 | 35000 | C10 | H | 6.2 |
| Example 10 | 35000 | C12 | H | 4.6 |

Each of the above gelatin derivatives was dissolved in 0.1M borate buffer having a pH of 9.5 at a concentration of 15 w/v %, and the solution thus obtained was placed in one of the two syringes of a 2.5 mL polypropylene disposable dual syringe and thereby each of the first agents was obtained.

<Preparation of the Second Agent>

As the second agent, pentaerythritol poly(ethylene)glycol ether tetrasuccinimidyl glutarate (4S-PEG, Sigma-Aldrich) was used. Just before the characterization described below, 4S-PEG was dissolved in a phosphate buffer having a pH of 4 and containing 100 μg/mL of brilliant blue in such an amount that a molar equivalent ratio of the succinimidyl ester group of 4S-PEG to the remaining amino group in the first agent was 0.2, 0.3 or 0.5, The solution thus obtained, was placed in the other syringe of the above dual syringe, and thereby each of the second agents was obtained.

<Sealing Strength Measurement I I>

Figure 11:
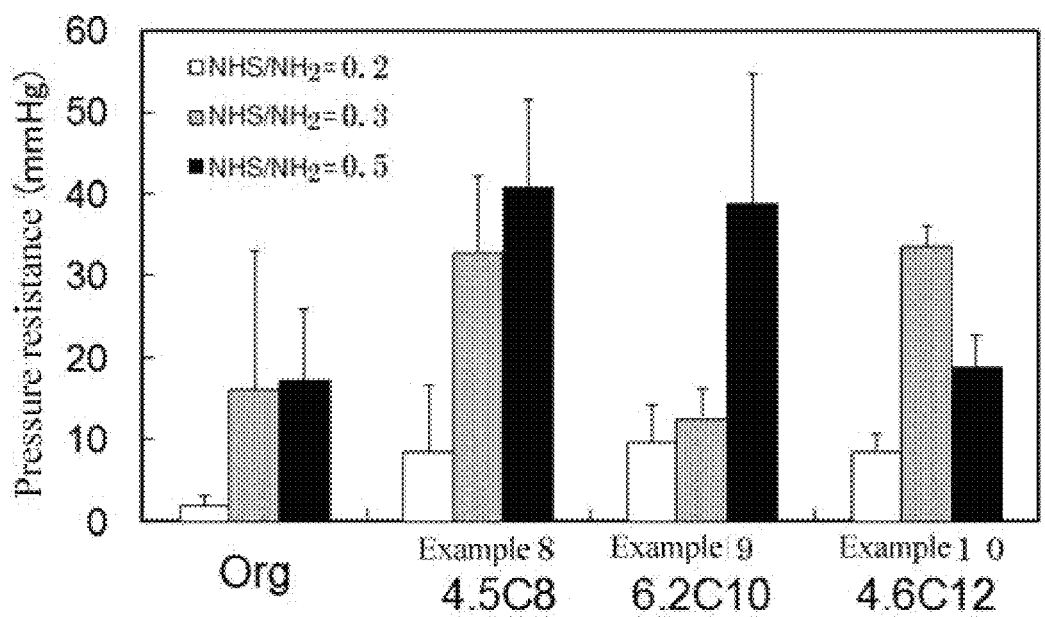
FIG. 11 is a graph showing burst strengths (mmHg) of the sealant membranes of Examples 8 to 10.

A sealing strength (pressure resistance) was measured by determining burst strength according to ASTM (F2392-04) by using the instrument schematically shown in FIG. 9 and porcine pulmonary pleura (φ30 mm) as the base material. A 1.0 mm-thick sealant membrane having a diameter of 15 mm was formed on the porcine pulmonary pleura by applying a mixture of 200 μL of the first agent and 200 μL of the second agent (equivalent of succinimidyl ester group in the crosslinking agent/equivalent of amino group in the gelatin derivative=0.5, 0.4, 0.3, or 0.2). Following the application, the sealant membrane was left to stand for 10 minutes. Then, saline at 37° C. was flowed at 2 mL/min and a pressure at bursting was measured. As a comparative example, the original gelatin was used. The results are shown in FIG. 11. In the figure, "NHS" represents equivalent amount of succinimidyl ester group, "NH₂" represents an amount of remaining amino group in the gelatin derivative, and "Org" represents an original gelatin, that is, underivatized gelatin.

As shown in FIG. 11, the strength of the membranes obtained from the sealants of Examples 8-10 was significantly higher than the original Alaska pollock-derived gelatin (Org) without the hydrophobic group even when NHS/NH₂ was 0.2, that is, a low degree of crosslinking. This difference was more significant at higher degrees of crosslinking. The strength depends on the number of carbon atoms of the hydrophobic group and the derivatization ratio, indicating that a much higher strength can be achieved by optimizing them.

INDUSTRIAL APPLICABILITY

The surgical sealant of the present invention can be prepared in an aqueous solvent in single step with a high yield and has an excellent resistance to electron beam sterilization. The membrane obtained from the sealant has a high adhesive strength to the tissues and sealing strength of the tissues in addition to low swelling by body fluid, so that it is highly suitable for surgical use.

What is claimed is:

1. A surgical sealant consisting of
   (1) a first agent comprising a gelatin derivative, wherein the gelatin derivative
      (a) has a weight average molecular weight of from 10,000 to 50,000;
      (b) has a hydrophobic group bonded thereto, the hydrophobic group being an alkyl group having 6 to 18 carbon atoms;
      (c) has a molar ratio of imino group/amino group of the gelatin derivative ranging from 1/99 to 30/70; and
      (d) comprises a structure represented by the following formula:

GltnNH—CHR¹R² 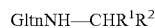

wherein "Gltn" represents a gelatin residue, R¹ is the hydrophobic group, and R² is a hydrogen atom or the hydrophobic group; and
   (2) a second agent comprising a crosslinking agent for the gelatin derivative, wherein said surgical sealant is resistant to radiation sterilization.

2. The surgical sealant according to claim 1, wherein the gelatin originates from a cold-water fish.

3. The surgical sealant according to claim 2, wherein the crosslinking agent is a polyethylene glycol ether polybasic acid ester.

4. The surgical sealant according to claim 2, wherein the cold-water fish is codfish.

5. The surgical sealant according to claim 4, wherein the crosslinking agent is a polyethylene glycol ether polybasic acid ester.

6. The surgical sealant according to claim 1, wherein the crosslinking agent is a polyethylene glycol ether polybasic acid ester.

7. The surgical sealant according to claim 1, wherein the first agent and the second agent are provided in such an amount that a ratio, (an equivalent amount of functional group of the crosslinking agent in the second agent/an equivalent amount of amino group in the gelatin derivative in the first agent), ranges from 0.2 to 2.

* * * * *